United States Patent [19]

Daigle

[11] Patent Number: 4,520,510

[45] Date of Patent: Jun. 4, 1985

[54] CONVERTIBLE HEADBAND CONSTRUCTION

[75] Inventor: Ronald H. Daigle, Cranston, R.I.

[73] Assignee: Wilbert Rosenberg, a part interest

[21] Appl. No.: 558,576

[22] Filed: Dec. 5, 1983

[51] Int. Cl.³ .............................................. A61F 9/02
[52] U.S. Cl. .......................................... 2/452; 2/454;
    2/426; 2/12; 2/15; 2/173; 2/207; 2/209.1;
    2/DIG. 11
[58] Field of Search ...................... 2/452, 454, 10, 12,
    2/13, 15, 426, 171, 171.5, 171.4, 171.8, 172, 173,
    183, 207, 209.1, 279, DIG. 11

[56] References Cited

U.S. PATENT DOCUMENTS

| | | | |
|---|---|---|---|
| 1,200,528 | 10/1916 | Ryder | 2/207 X |
| 1,289,766 | 12/1918 | Hook | 2/207 X |
| 1,650,258 | 11/1927 | Bloomfield | 2/173 |
| 1,807,475 | 5/1931 | Gibson | 2/15 |
| 2,126,379 | 8/1938 | Fischer | 2/452 X |
| 2,682,667 | 7/1954 | Michelstetter | 2/207 X |
| 2,778,025 | 1/1957 | Burrows | 2/207 |
| 3,260,292 | 7/1966 | Costello | 2/209.1 X |
| 3,378,851 | 4/1968 | McBrayer | 2/454 |
| 4,365,354 | 12/1982 | Sullivan | 2/DIG. 11 |
| 4,393,519 | 7/1983 | Nicastro | 2/DIG. 11 |

Primary Examiner—Henry S. Jaudon
Assistant Examiner—J. L. Kravitz
Attorney, Agent, or Firm—Salter & Michaelson

[57] ABSTRACT

A headband construction is convertible for use, in the alternative, as a conventional headband or as a pair of sunglasses or sunshields. The headband construction includes an elongated band having a pair of eye openings therethrough which is receivable in encircling relation on the head of a wearer, a flap which is attached to the band adjacent the eye openings, and a lens piece which is secured on the band covering the eye openings. The flap is alternately positionable in a first position thereof wherein it is received and detachably retained in a wrapped disposition on the band so that it covers the eye openings and the lens piece, or a second position thereof wherein it is retained in a rolled or folded disposition adjacent the band so that it extends longitudinally therealong but does not obstruct the lens piece or the eye openings. The headband can also be worn with the flap in the second position thereof with the lens piece removed to provide a retainer for a pair of conventional eyeglasses.

10 Claims, 13 Drawing Figures

U.S. Patent Jun. 4, 1985 Sheet 1 of 4 4,520,510
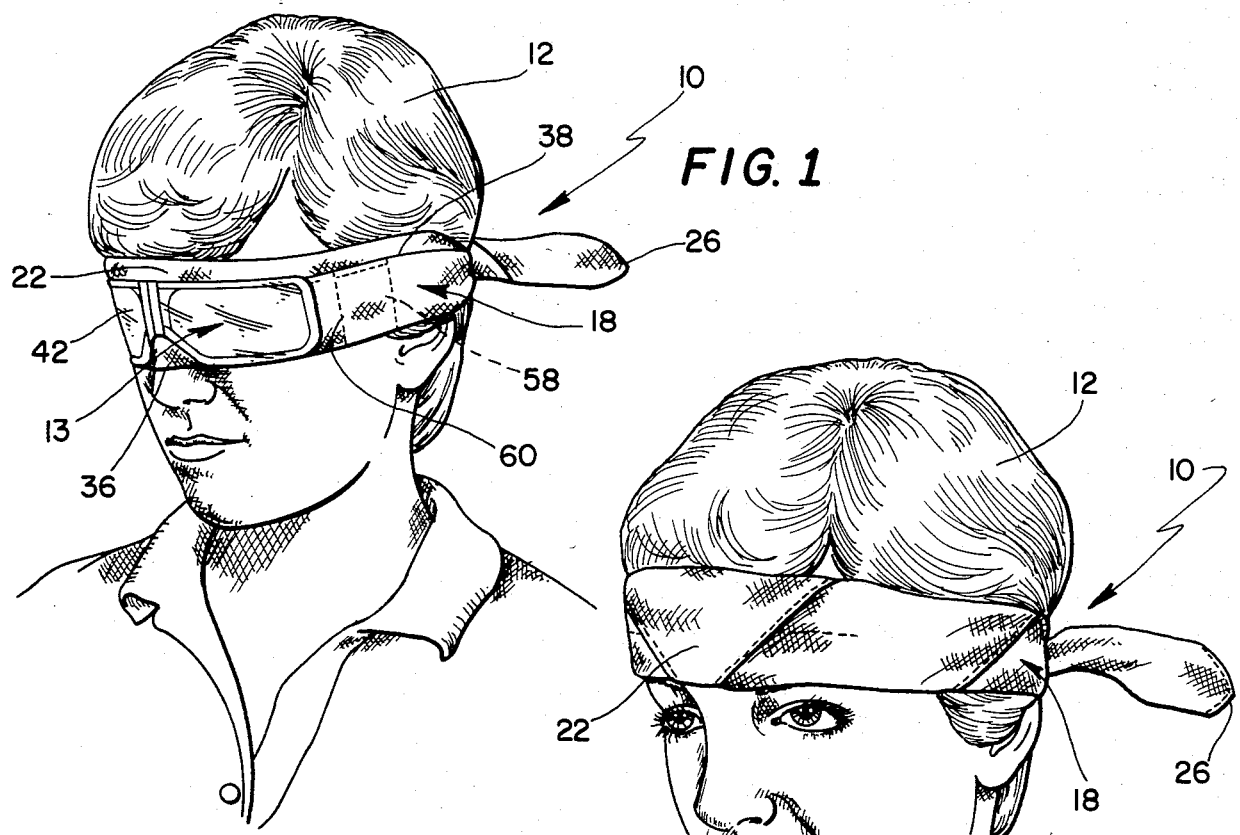
FIG. 1
FIG. 2
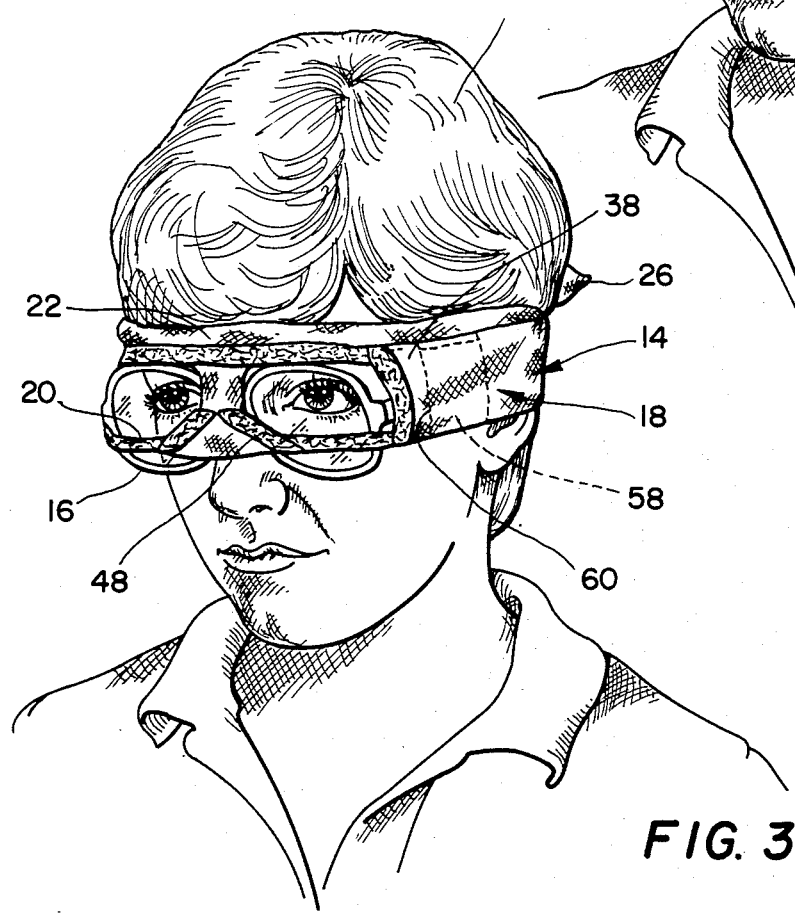
FIG. 3

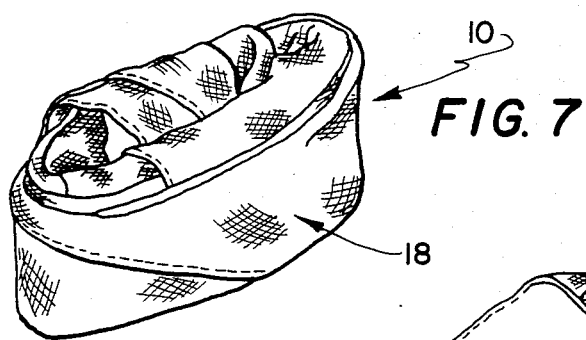
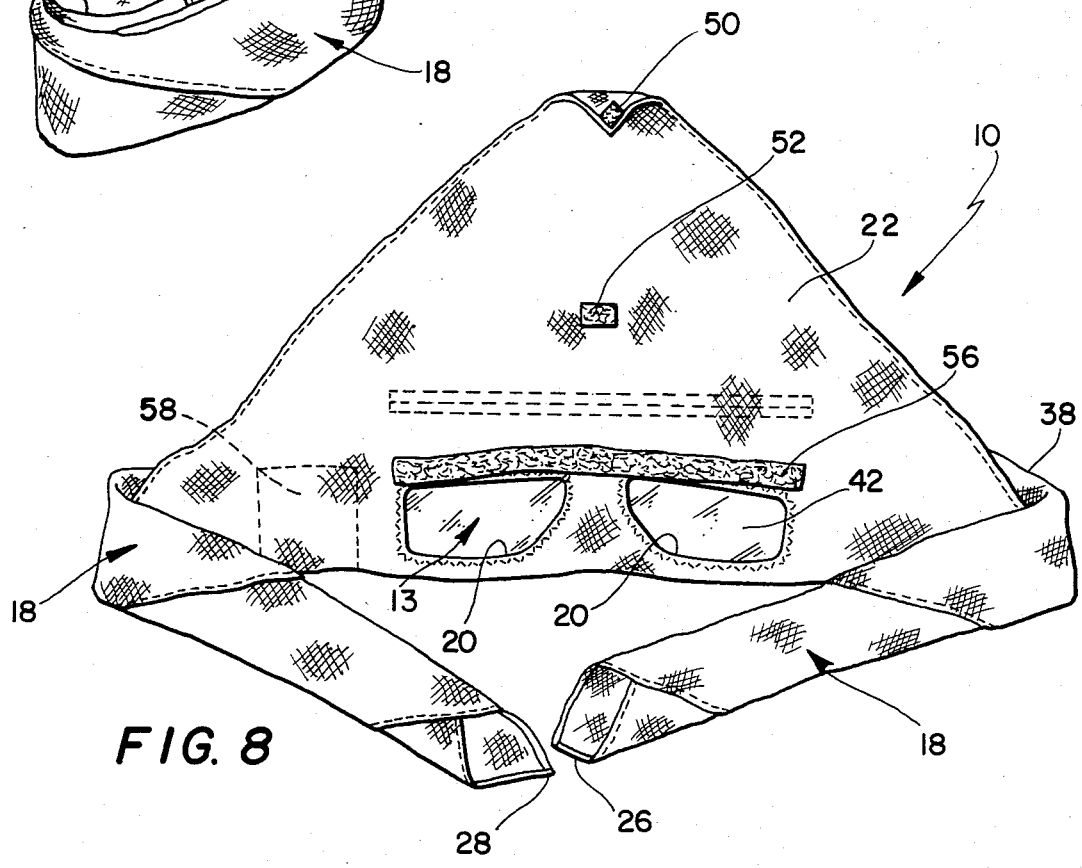
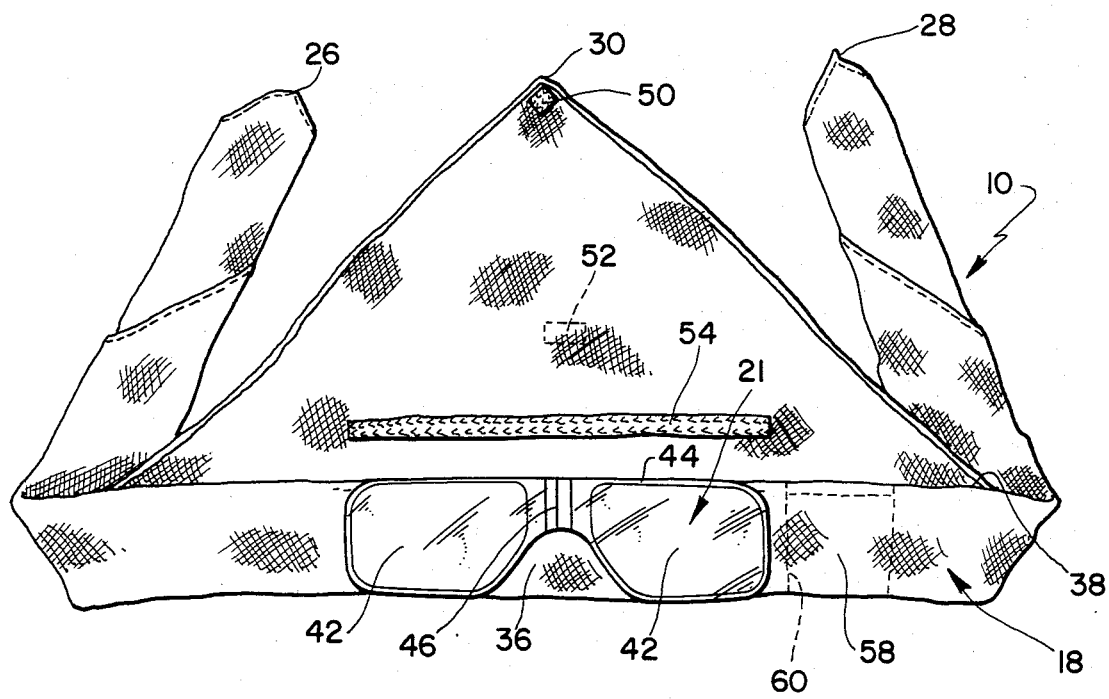

CONVERTIBLE HEADBAND CONSTRUCTION

BACKGROUND AND SUMMARY OF THE INVENTION

The instant invention relates to a novel headband construction which is convertible so that it can be worn, in the alternative, as a conventional headband, as a pair of sunglasses or sunshields, or as a retainer for conventional eyeglasses.

The wearing of sunglasses or sunshields has become highly popular for virtually all outdoor activities. It is also generally known to wear sunglasses or sunshields, as well as conventional eyeglasses, in combination with retainer straps and the like during strenuous or rigorous physical activities to securely retain the sunglasses or sunshields or conventional eyeglasses on the head of a wearer. In recent years the wearing of headbands has also become relatively popular, and a wide variety of headband constructions have become available for use as articles of ornamentation or for more practical reasons, particularly during rigorous physical activity, such as for retaining the hair to prevent it from interfering with the eyes, or for absorbing perspiration.

While sunglasses or sunshields, headbands and eyeglass retainers have heretofore been available as separate components, a single device which is convertible for use, in the alternative, as a pair of sunglasses or sunshields, as a headband or as a retainer for eyeglasses is unknown in the prior art. The instant invention provides such a device comprising an elongated flexible band which is snugly receivable in encircling relation on the head of a wearer having a pair of eye openings therethrough, and a flexible flap attached to the band or forming a continuation thereof. The flap is alternately positionable in a first position thereof wherein it is wrapped around the band for covering the eye openings and a second position thereof wherein it is disposed adjacent the band but the eye openings are unobstructed so that the band is receivable on the head of a wearer with the eye openings aligned with the eyes of the wearer. Means are provided in the headband construction for selectively retaining the flap in the first or second positions thereof; and, in the preferred embodiment, a lens piece, which is at least partially flexible, is detachably secured on the band so that it substantially covers the eye openings. Also in the preferred embodiment, the headband is constructed from a flexible fabric piece, such as a bandana, having a substantially triangular portion, which is folded so that a pair of the corners of the triangular portion define opposite ends of the band, and a triangular flap which integrally extends from the band, the unattached corner of the triangular flap being defined by the third corner of the triangular portion of the fabric sheet. Accordingly, it is seen that by positioning the flap in the first position thereof wherein it covers the eye openings and the lens piece and tying or otherwise interconnecting the ends of the band, the headband construction can be worn as a conventional headband or as a neckkerchief. However, by moving the flap to the second position thereof wherein the eye openings and the lens piece are unobstructed, the headband can be worn as a pair of eyeglasses, or sunglasses or sunshields when the lens piece is appropriately colored. As a third alternative, the headband construction can be worn with the flap in the second position thereof and with the lens piece removed from the band to retain a pair of eyeglasses on a wearer. Specifically, the headband construction can be worn in this manner with the eye openings aligned with the eyes of a wearer so that the portions of the band adjacent the eye openings engage the frame and the peripheral portions of the lenses of a pair of eyeglasses to retain the glasses on the head of a wearer.

The closest prior art to the instant invention of which the applicant is aware is disclosed in U.S. patents to Stangl U.S. Pat. No. 150,474; Tilton U.S. Pat. No. 178,328; Holly et al U.S. Pat. No. 198,474; Gould U.S. Pat. No. 207,187; Sameth U.S. Pat. No. 2,491,137; Gross et al U.S. Pat. No. 3,173,147; McBrayer U.S. Pat. No. 3,378,851; and Van Tiem et al U.S. Pat. No. 4,152,051. While these references disclose a variety of eyeglass and goggle constructions, including some which are embodied with headbands and the like, they clearly do not suggest a combination headband construction which embodies the novel structural features of the instant invention and which is adaptable for a variety of different uses. Hence, the above references are believed to be of nothing more than general interest.

Accordingly, it is a primary object of the instant invention to provide a convertible headband construction which can be worn in the alternative as a conventional headband or as a pair of sunglasses or sunshields.

A further object of the instant invention is to provide a combination headband construction which can be worn as a headband, as a pair of sunglasses or sunshields, or as an eyeglass retainer.

Another object of the instant invention is to provide a novel headband construction which can be worn as a headband having the appearance of a conventional bandana or, in the alternative, worn as a pair of sunglasses or sunshields.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of the convertible headband construction of the instant invention worn as a pair of sunglasses or sunshields;

FIG. 2 is a perspective view thereof worn as a headband;

FIG. 3 is a perspective view thereof worn as an eyeglass retainer;

FIG. 7 illustrates a folded configuration of the headband construction;

FIG. 8 is a rear perspective view of the headband construction in an open configuration;

FIG. 9 is a similar front perspective view thereof;

DESCRIPTION OF THE INVENTION

Figure 4:
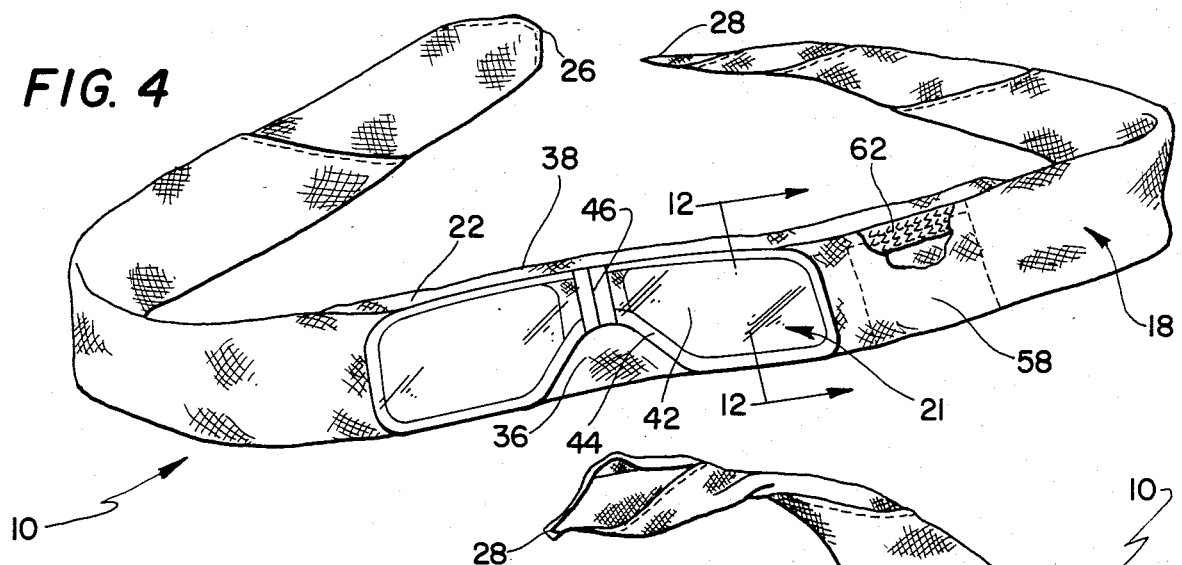
FIG. 4 is a perspective view of the headband construction per se adapted for use as a pair of sunglasses or sunshields.

Referring now to the drawing, a first embodiment of the convertible headband construction of the instant invention is illustrated and generally indicated at 10 in FIGS. 1, 2, 4 through 9, 12 and 13. The headband 10 is adapted to be worn on a head 12 of a wearer, in the alternative, as a pair of sunglasses or sunshields, as illustrated in FIG. 1, or as a headband, as illustrated in FIG. 2. Further, upon removal of a lens piece 13 from the headband 10 in a manner which will hereinafter be made apparent, an eyeglass retainer 14 is formed as illustrated in FIG. 3 which is adapted to be worn on the head 12 of the wearer for retaining a pair of eyeglasses 16 thereon.

Figure 5:
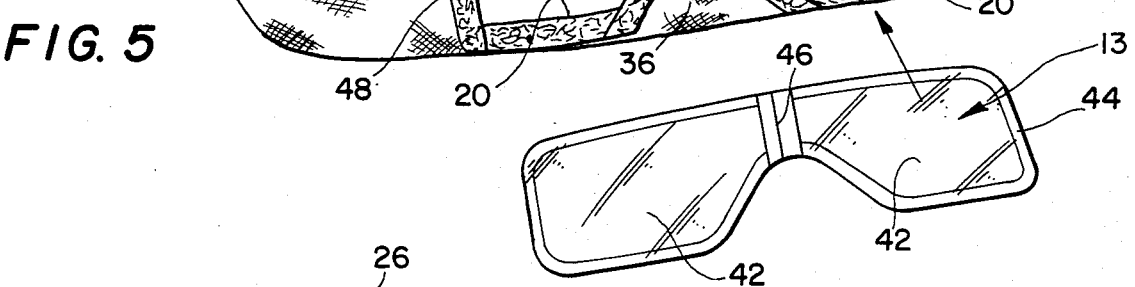
FIG. 5 is a similar view thereof with the lens piece removed.
Figure 6:
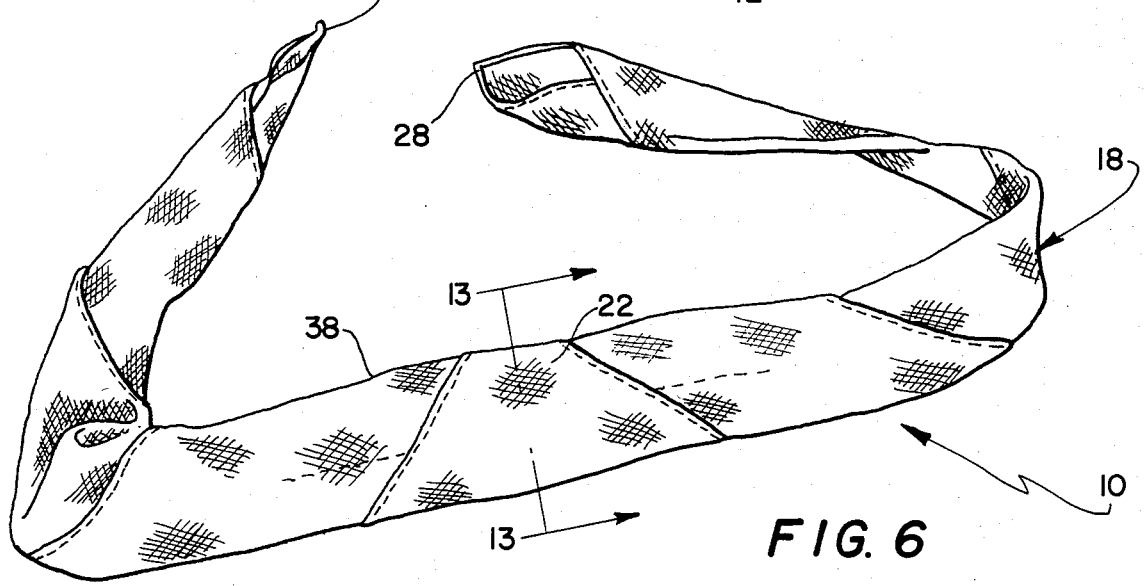
FIG. 6 is a perspective view of the convertible headband construction adapted for use as a headband.

Referring to FIGS. 6, 7, 8 and 9, the convertible headband 10 comprises an elongated band 18, having a pair of eye openings 20 therein, the lens piece 13 which is detachably secured in substantially covering relation over the eye openings 20, and a flap 22 which is attached to the band 18 and which is alternately positionable in a first position thereof illustrated in FIG. 6, wherein it is received on the band 18 for covering the lens piece 21, and a second position thereof wherein it is disposed adjacent the band 18 but does not obstruct the openings 20 or the lens piece 21. More specifically, when the flap 22 is in the first position thereof, it is received in a wrapped or encircling relation around the band 18 and thereby covers the lens piece 21 and the openings 20 as illustrated in FIG. 6. When the flap 22 is in this position, the flap 22 and the band 18 cooperate to define a strap-like headband as illustrated in FIGS. 2 and 6. When the flap 22 is in the alternate second position thereof, it is rolled or folded to an elongated configuration so that it is disposed adjacent the band 18 and extends substantially longitudinally therealong so that the openings 20 are unobstructed, as illustrated in FIG. 5. Means which will hereinafter be more fully described are also provided in the headband 10 for alternately detachably retaining the flap 22 in the first and second positions thereof.

Figure 10:
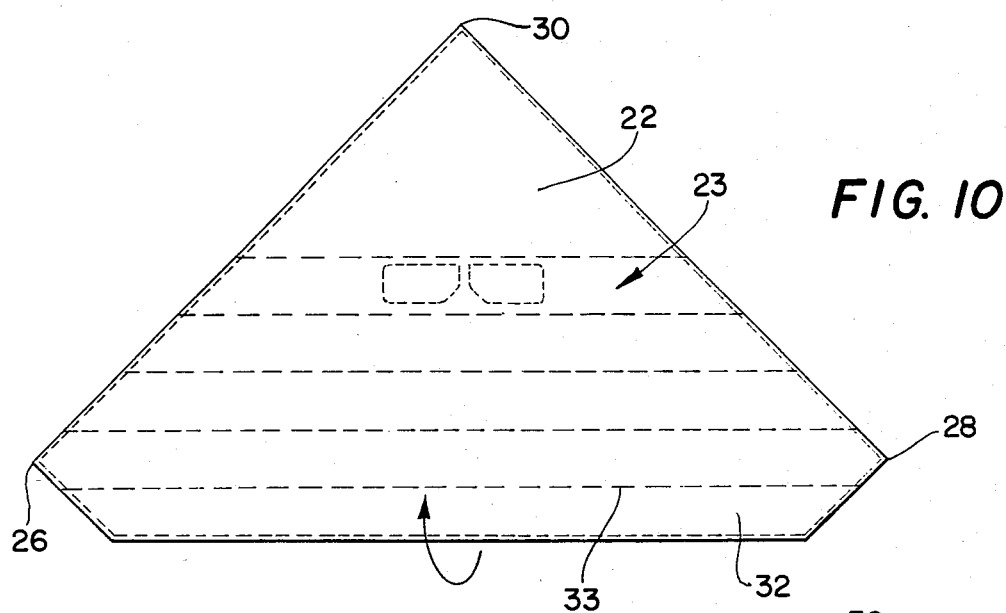
FIG. 10 is a top plan view of a fabric sheet prior to the folding thereof on itself to define band and flap portions of the headband construction of the instant invention.
Figure 11:
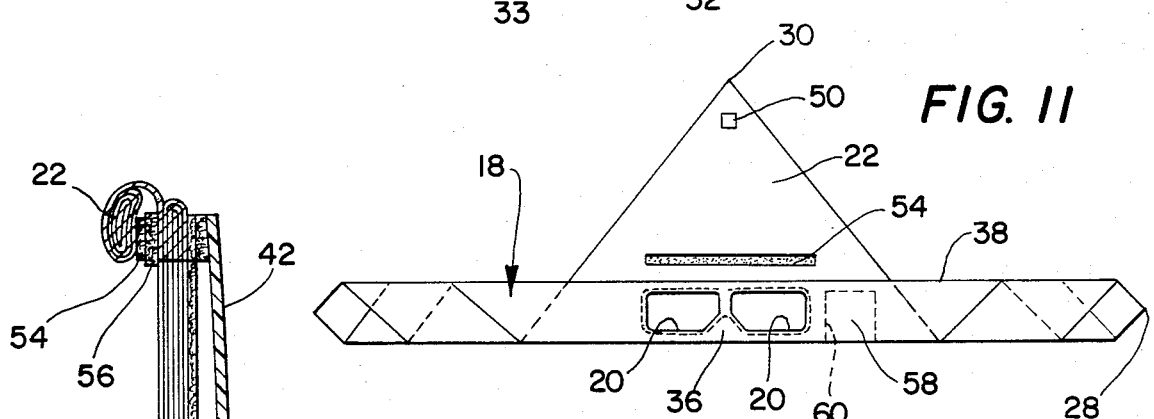
FIG. 11 is a top plan view of the sheet after it has been formed to define band and flap portions, the sheet also having retaining means and pocket means thereon.
Figure 12:
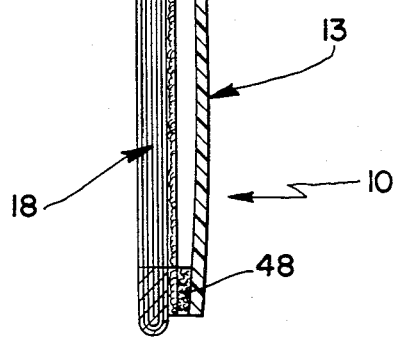
FIG. 12 is a sectional view taken along line 12—12 in FIG. 4.
Figure 13:
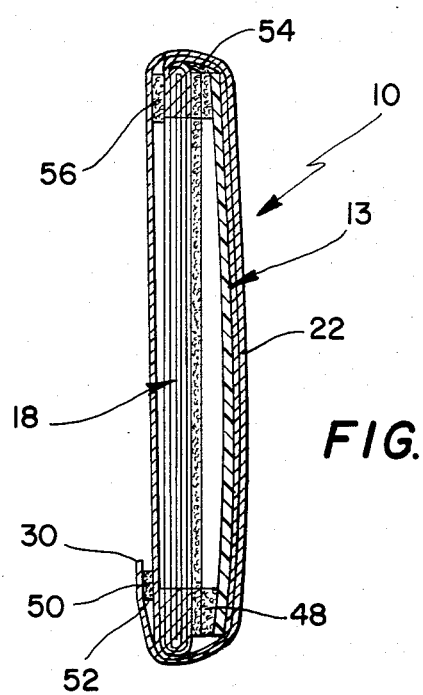
FIG. 13 is a sectional view taken along line 13—13 in FIG. 6.

Referring now to FIGS. 10 and 11, the construction of the band 18 and the flap 22 is more clearly illustrated. In this connection, and as will be seen from FIG. 10, the flap 22 and the band 18 are preferably formed from a single flexible sheet of fabric 23, such as a bandana or a portion thereof, having a substantially triangular portion 24 which includes first, second and third corners 26, 28 and 30, respectively. In the embodiment herein illustrated, the sheet 23 also includes a trapezoidal portion 32, although other constructions of the band 10 are contemplated which include sheets which are of entirely triangular configurations or of other different configurations. In any case, in the band 10, as herein embodied, the sheet 23 is folded over on itself a plurality of times in the manner illustrated in FIG. 10 along foldlines 33 to define the flap 22 and the elongated band 18 which comprises a plurality of layers of fabric which has been folded over on itself toward the corner 30, so that the ends of the band are defined by the corners 26 and 28. When the fabric sheet 23 is folded in this manner to define the band 18, the flap 22 is formed in a triangular configuration wherein the third corner 30 defines the unconnected corner of the flap 22. After the sheet 23 has been folded in the above-described manner, the eye openings 20 are formed therein, so that they extend through the multiple layers of fabric in the central portion of the band 18. Stitching 34 around the peripheries of the openings 20 maintains the openings in the various layers of fabric in proper alignment and also prevents the unfolding of the band 18. In the preferred embodiment of the instant invention, the openings 20 are formed in the configuration of conventional eyeglass lenses and define a nose area 36 on the band 18 which is formed to be received over the bridge of the nose of a wearer. In this regard, it will be understood, however, that the embodiment of the headband of the instant invention so that the two openings 20 are interconnected and therefore actually defined by a single large opening is also contemplated. The flap 22 preferably extends integrally from the upper edge 38 of the band 18 in the area of the eye openings 20 as illustrated in FIG. 11. It should be pointed out that while the band 18 and the triangular flap 22 are integrally formed from a fabric sheet 23 which has been folded in the manner hereinabove described, other embodiments of the invention which include bands and flaps of other constructions and configurations are contemplated. Further, the construction of bands and/or flaps from diverse materials, including various fabrics, furs, and other flexible materials, is also contemplated.

The lens piece 21 preferably comprises a pair of colored transparent lens elements 42 which are preferably constructed of an at least partially flexible plastic material and which have opaque peripheral rims 44. The lens elements 42 are preferably hingedly interconnected along a foldline 46 so that they can be folded for storage of the headband 10. Preferably the lens piece 21 is detachably secured on the band 18 with conventional nylon hook-and-loop-type fastening elements, such as Velcro (Velcro USA Inc. T.M.) or the like. In this connection, fastening strips 48 are permanently attached to the band 18 around the peripheries of the openings 20, and mating fastening strips (not shown) are provided on the rear side of the rims 44 for detachably securing the lens piece 21 on the band 18.

Referring now to FIGS. 8 and 9, the means provided for alternately detachably retaining the flap 22 in the first or second positions thereof is more clearly illustrated. Specifically, in the preferred embodiment, hook-and-loop-type fastening patches 50 and 52 are provided for detachably retaining the flap 22 in the first position thereof wherein it is wrapped around the band 18 to cover the lens piece 21. In this regard, the patch 50 is disposed adjacent the unattached corner 30 on the side of the flap 22 which faces outwardly when the flap 22 is in an unattached, outwardly extending disposition, as illustrated in FIGS. 8 and 9. The patch 52 is disposed in the central portion of the flap 22 on the opposite side thereof from the patch 50 and is positioned so that when the flap 22 is wrapped around the band 18, the patches 50 and 52 meet to detachably retain the flap 22 in a wrapped disposition. In order to retain the flap 22 in the second position thereof wherein it is in a rolled-up or folded disposition and extends substantially longitudinally along the band 18 on the rearside thereof, fastening strips 54 and 56 are provided. The strip 54 is disposed on the side of the flap 22 which faces outwardly when the flap 22 is in the outwardly extended, unattached disposition thereof illustrated in FIG. 9 and extends in substantially parallel spaced relation to the upper edge 38 of the band 18, whereas the strip 56 extends along the rear side of the band 18 adjacent the upper edges 38 thereof. By rolling the flap 22 toward the band 18, the strip 54 is positionable in mating relation with the strip 56 to detachably retain the flap 22 in the second position thereof wherein it extends substantially longitudinally along the rear side of the band 18 adjacent the upper edge 38 thereof.

Also provided in the headband 10 is a pocket 58 which is formed in the band 18 adjacent the eye openings 20. In this regard, the pocket 58 is formed between the two forwardmost layers of the sheet 23 and is defined by stitching 60, and hook-and-loop-type fastening components 62 illustrated in FIG. 4 are provided at the upper edge of the pocket 58 for detachably retaining it in a closed position.

The headband 10 can, therefore, either be worn as a pair of sunglasses or sunshields, as illustrated in FIG. 1, or as a headband as illustrated in FIG. 2. In addition, by removing the lens piece 21 from the band 18 and positioning the flap 22 in the second position thereof wherein it is in a rolled or folded disposition and extends along the upper edge 38 of the band 18, an eyeglass retainer 14 is formed which can be worn in the manner illustrated in FIG. 3. In this connection, the band 18 is securely retained in encircling relation on the head 12 of a wearer simply by tying the two ends of the band 18 together in the rear of the head 12. Other embodiments of the headband construction of the instant invention are also contemplated, however, which include continuous loop-type bands or alternate means for interconnecting the free ends of bands. When either the headband 10 or the eyeglass retainer 14 is worn with the flap 22 in the second position thereof adjacent the band 18, the flap 22 provides a cushion along the upper edge of the band 18 to provide enhanced wearer comfort. When the headband 10 is worn as a pair of sunglasses or sunshields, a novel and stylish effect is achieved, and the sunglasses or sunshields are securely retained on the head 12 even during rigorous physical activity. When the headband 10 is worn with the flap 22 in the first position thereof wherein it is wrapped around the band 18, a conventional headband is provided which can be worn in the manner illustrated in FIG. 2. It will be understood, however, that the band 10 can also be worn with the flap 22 in this position as a neckerchief or the like. The pocket 58 provides a convenient place for storage of small articles, such as coins, keys and the like. In addition to the above, the headband 10 may be simply and easily folded to the configuration illustrated in FIG. 7 for storage by folding the band 18 along the hinge line 46 of the lens piece 13, wrapping the two ends of the band 18 around the folded center portion thereof, and tucking the outer end of the band 18 into the center of the folded band 18.

It is seen, therefore, that the instant invention provides a novel and effective convertible headband construction which can be worn in the alternative as a pair of sunglasses or sunshields, as a headband, or as an eyeglass retainer. The band 10 can be comfortably worn during even the most rigorous physical activity. Further, the headband construction of the instant invention is stylish as well as practical. Accordingly, for these reasons, as well as the other reasons hereinabove set forth, the headband construction of the instant invention represents a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A convertible headband construction comprising:
    a. an elongated flexible band receivable in snugly encircling relation on the head of a wearer, said band having an eye opening therethrough;
    b. a flexible flap on said band, said flap being alternately positionable in a first position thereof wherein it is received in encircling relation around said band for covering said eye opening and wherein said flap and said band cooperate to define a strap-like headband, and a second position thereof wherein said flap is disposed adjacent said band but said eye opening is unobstructed, and wherein said band is receivable on said head so that said eye opening is aligned with an eye of said wearer;
    c. means for detachably retaining said flap in said first position thereof; and
    d. means for alternatively detachably retaining said flap in said second position thereof.

2. In the headband construction of claim 1, said band further characterized as having first and second ends which are detachably interconnectable to secure said band in encircling relation on the head of said wearer.

3. The headband construction of claim 1 further comprising a flexible lens piece secured on said band substantially covering said eye opening, said flap substantially covering said lens piece when said flap is in said first position thereof.

4. In the headband construction of claim 1, said means for securing said flap in said second position thereof further characterized as securing said flap in an elongated folded configuration wherein it extends longitudinally along said band.

5. In the headband construction of claim 2, said band and said flap being integrally formed from a sheet of flexible material having a substantially triangular portion, said sheet being folded on itself a plurality of times to define an elongated band of folded material and a substantially triangular flap which is attached to said band along one edge of said flap, a pair of the corners of said triangular portion defining the opposite ends of said band and the third corner of said triangular portion defining an unattached corner of said flap.

6. In the headband construction of claim 5, said sheet further characterized as being formed from a bandana.

7. In the headband construction of claim 3, said lens piece being detachably secured on said band.

8. The headband construction of claim 1 further comprising pocket means on said band.

9. In the headband construction of claim 3, said elongated flexible band having a pair of eye openings therein, said lens piece comprising a pair of hingeably interconnected individual lens elements, one of said lens elements covering each of said eye openings.

10. In the headband construction of claim 4, said band further characterized as having upper and lower edges and front and rear sides, said rear side facing the head of said wearer when said band is received thereon, said flap extending along the upper rear side of said band when said flap is in said second position thereof to provide a cushion on said band which engages the head of said wearer when said band is received thereon.

* * * * *